(12) United States Patent
Carstensen et al.

(10) Patent No.: US 6,615,671 B1
(45) Date of Patent: Sep. 9, 2003

(54) METHOD FOR DETERMINING THE FATIGUE STRENGTH OF A CORRODIBLE CONNECTING PART

(75) Inventors: Hartmut Carstensen, Berlin (DE); Reinhard Knödler, Sandhausen (DE); Rainer Franke, Pirna (DE)

(73) Assignee: DaimlerChrysler Rail Systems GmbH, Berlin (DE)

( * ) Notice: Subject to any disclaimer, the term of this patent is extended or adjusted under 35 U.S.C. 154(b) by 0 days.

(21) Appl. No.: 09/890,773

(22) PCT Filed: Feb. 28, 2000

(86) PCT No.: PCT/EP00/00658
§ 371 (c)(1),
(2), (4) Date: Jan. 28, 2002

(87) PCT Pub. No.: WO00/46587
PCT Pub. Date: Aug. 10, 2000

(30) Foreign Application Priority Data

Feb. 3, 1999 (DE) .......................................... 199 05 283
Dec. 18, 1999 (DE) .......................................... 199 63 313

(51) Int. Cl.⁷ ............................................... G01N 3/32
(52) U.S. Cl. ....................................................... 73/808
(58) Field of Search .......................... 73/760, 766, 785, 73/787, 789, 795, 856, 848, 808, 810, 850, 851

(56) References Cited

U.S. PATENT DOCUMENTS

| | | | | |
|---|---|---|---|---|
| 4,090,401 A | * | 5/1978 | Yamamoto et al. | 73/808 |
| 4,920,807 A | * | 5/1990 | Stokes et al. | 73/808 |
| 5,305,645 A | * | 4/1994 | Reifsnider et al. | 73/808 |
| 5,852,246 A | * | 12/1998 | Fiedler et al. | 73/811 |
| 6,193,816 B1 | * | 2/2001 | Nakano et al. | 148/333 |
| 6,532,657 B1 | * | 3/2003 | Weimer et al. | 29/889.2 |

OTHER PUBLICATIONS

Lachmann E: "Durability of Bonded Metal Joints in Motor Vehicle Construction" Vide Couches Minces, N.. 272, Supp. S, Aug. 1994; pp. 277–283.

Oue Y. et al, "Dependence of Corrosion Fatigue Behaviour of Friction–Welded Butt Joints on Friction Welding Procedure"; Welding International, GB, Welding Institute, Abington, vol. 10. No. 3, Jan. 1, 1996; pp. 207–214.

Flossdorf, et al, "Fatigue strength of weathering structural steels after many years of atmospheric exposure" Stahl Und Eisen, DE, Verlag Stahleisen GmbH, Dusseldorf, vol. 117. No. 11, pp. 105–111.

Charalambides M N, et al, "Adhesively–bonded repairs to fibre–composite materials I. Experimental"; Composites, GB, IPC Business Press Ltd. Haywards Heath, vol. 29, No. 11., Nov. 1, 1998. pp. 1371–1381.

* cited by examiner

Primary Examiner—Edward Lefkowitz
Assistant Examiner—Andre Allen
(74) Attorney, Agent, or Firm—Venable LLP; Norman N. Kunitz

(57) ABSTRACT

A method for determining the fatigue strength of a corrodible connecting part between at least two structural parts, with the connecting part being subjected to specified corroding surroundings and a given repeated mechanical strain while being used. Diagrams (stress-number curves) that represents the variable of the repeated strain in relation to the number of strain repetitions until the destruction of the connecting part are used in order to determine the fatigue strength. First, a strain-free pre-corrosion of the connecting parts is carried out in a corrosive atmosphere corresponding to the corrosive atmosphere during the intended use of the part, in a time period after which the duration of the pre-corrosion has hardly any influence on the shape of a stress-number curve that is recorded subsequently. The pre-corrosion connecting part is then subjected to a given repeated mechanical strain in surroundings which match the specific corroded surroundings in order to record a stress-number curve until the fatigue strength has been reached. The pre-corrosion is preferably carried out at a temperature which is higher than ambient temperature, whereby the duration of the pre-corrosion can be significantly reduced.

11 Claims, 7 Drawing Sheets

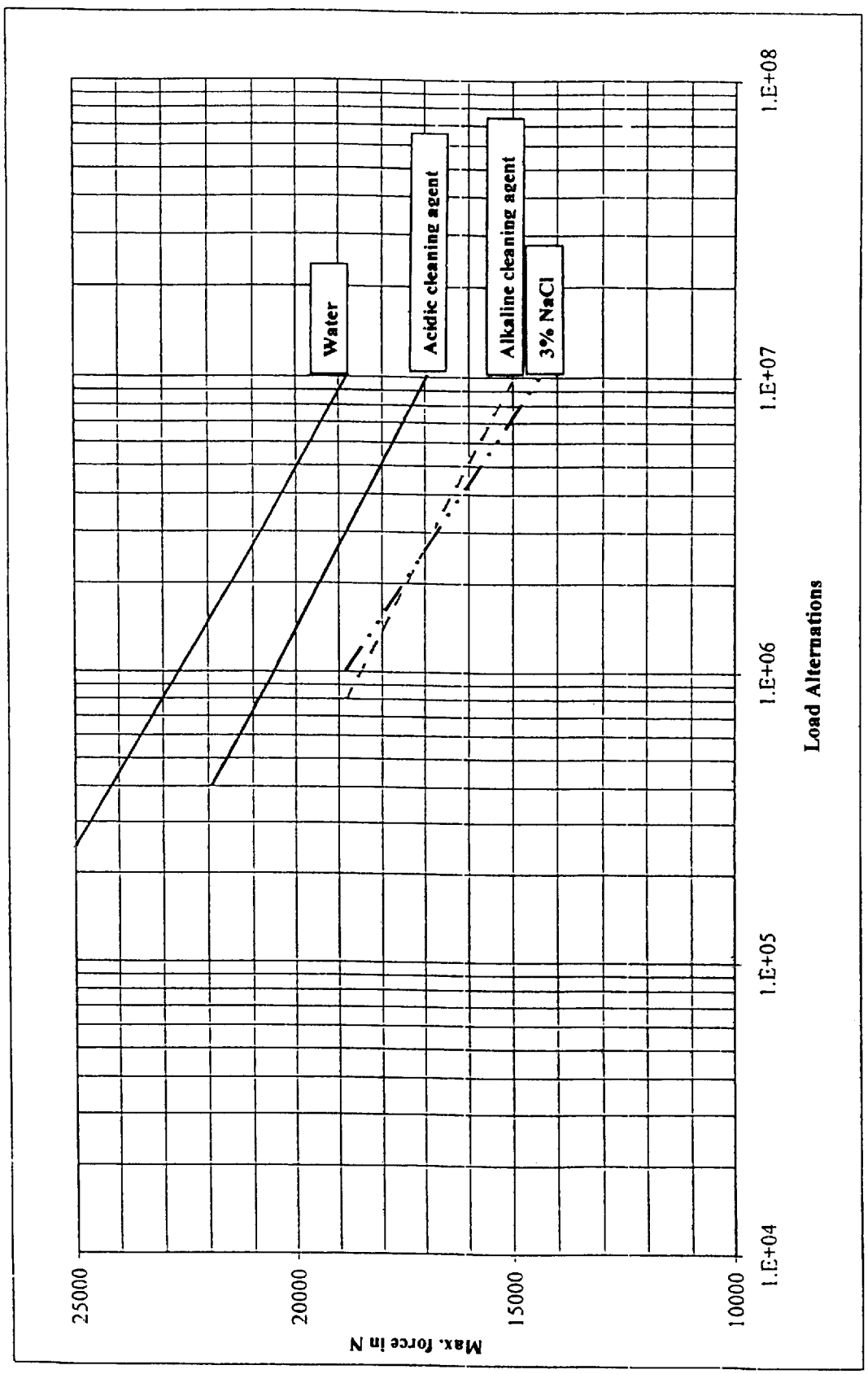
Fig. 3: Stress-number curves in different corrosive media without pre-corrosion

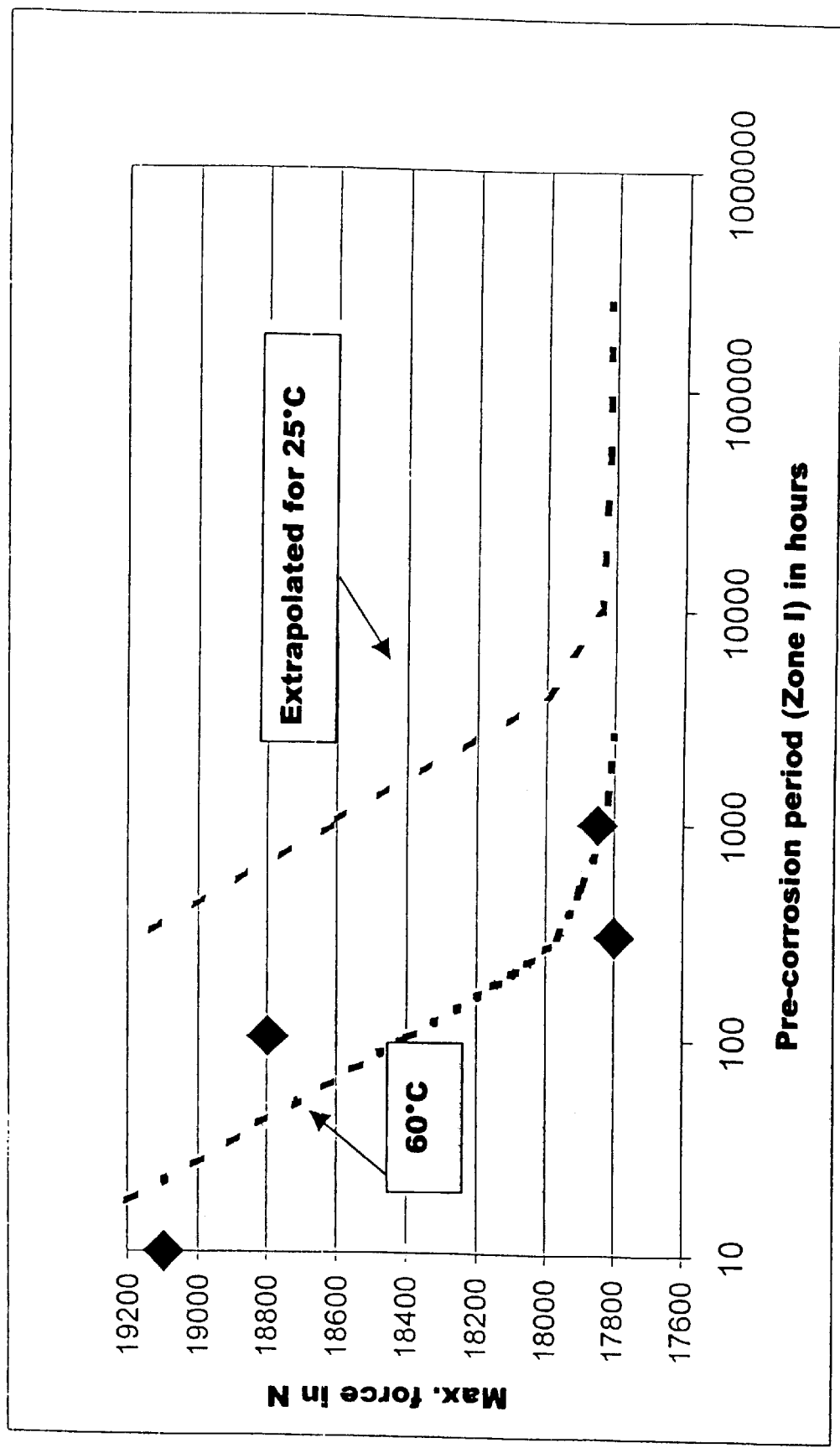
Fig. 4: Influence of the pre-corrosion period (Zone I: 90% air humidity with condensation) on the fatigue strength, with extrapolation for room temperature

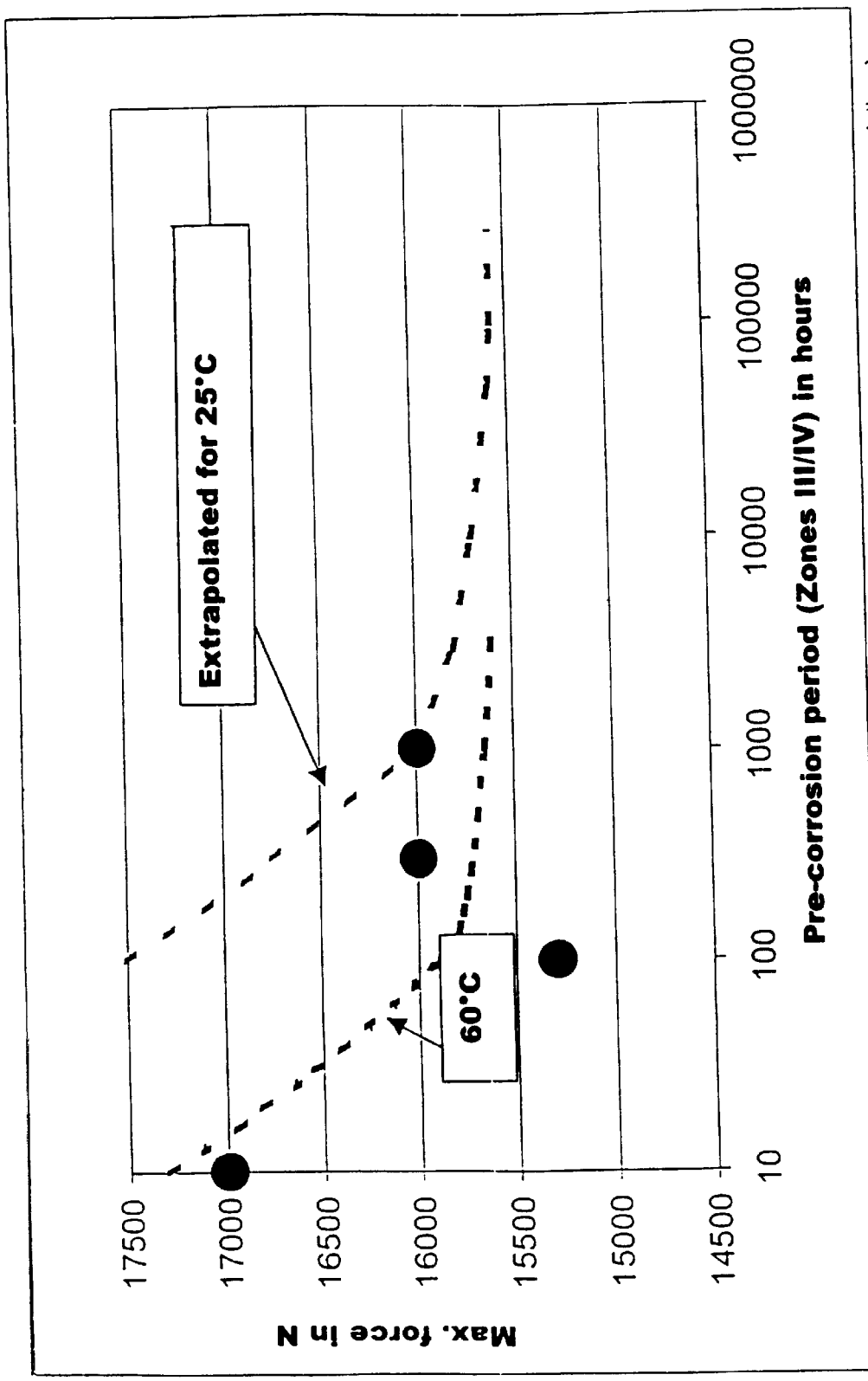
Fig. 5: Influence of the pre-corrosion period (Zones III/IV: $SO_2$-containing atmosphere with 90% air humidity and cleaning solutions) on the fatigue strength, with extrapolation for room temperature

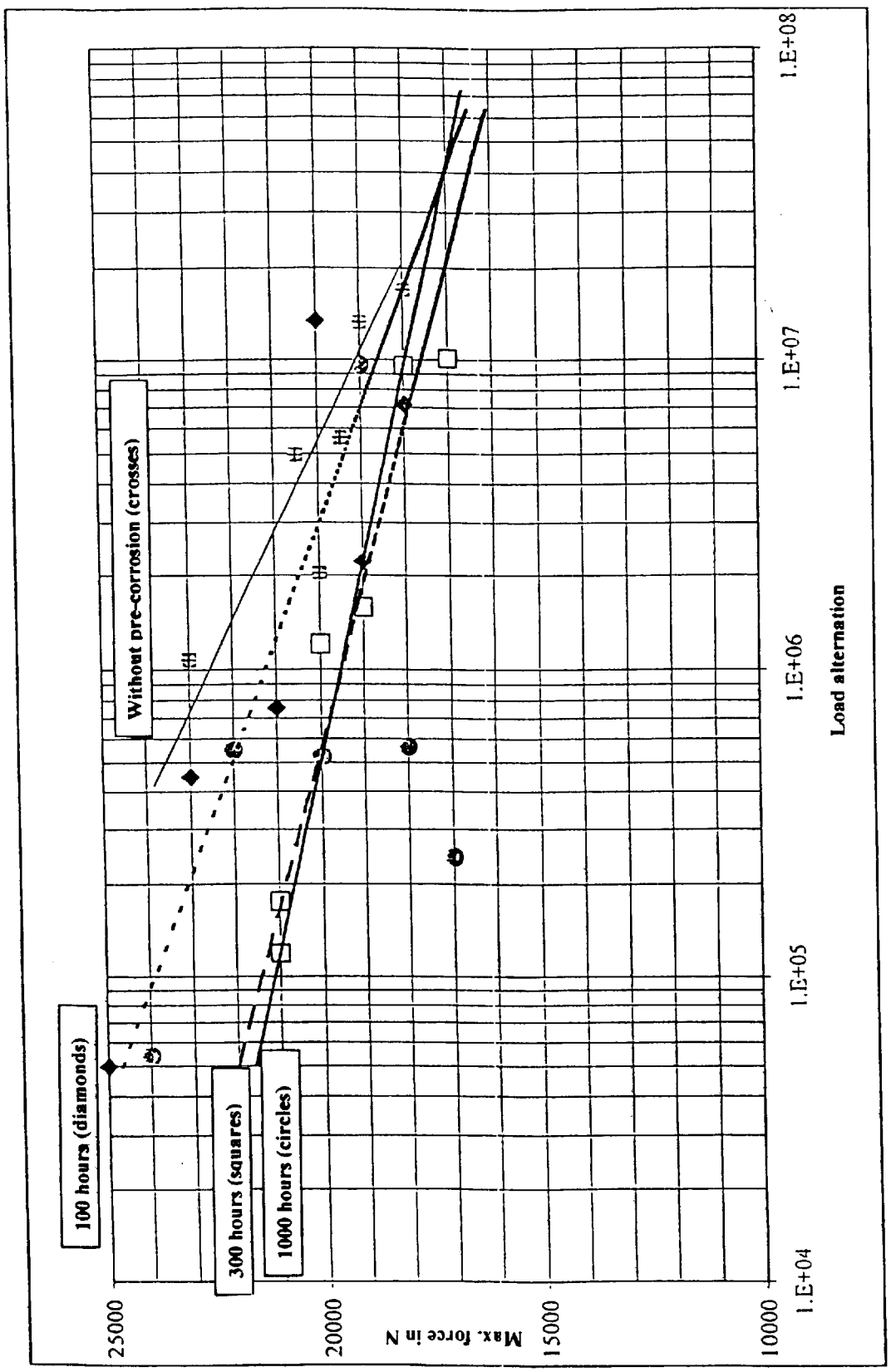
Fig. 6: Stress-number curves (Zone I) for different pre-corrosion periods

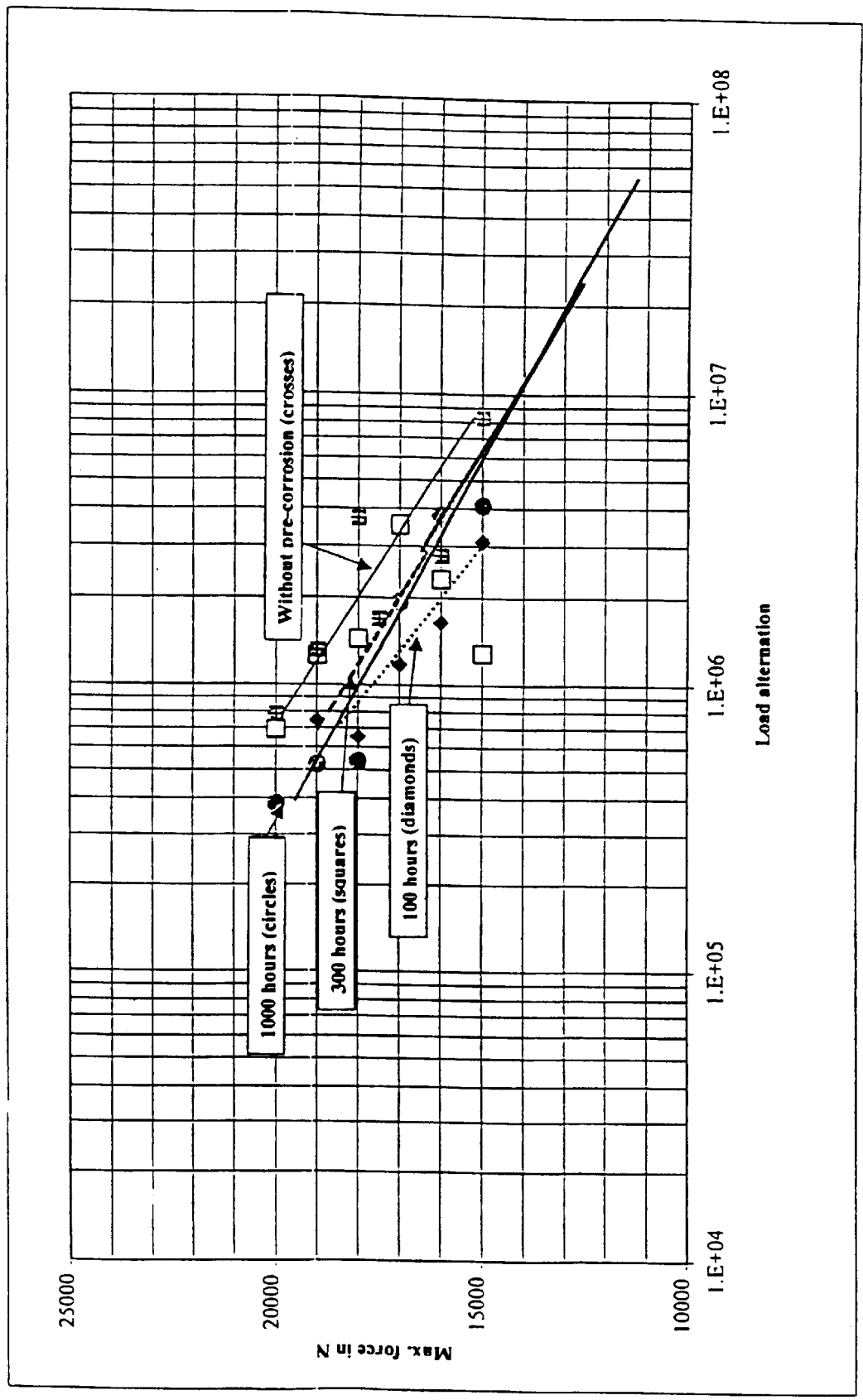
Fig. 7: Stress-number curves (Zones III/IV) for different pre-corrosion periods

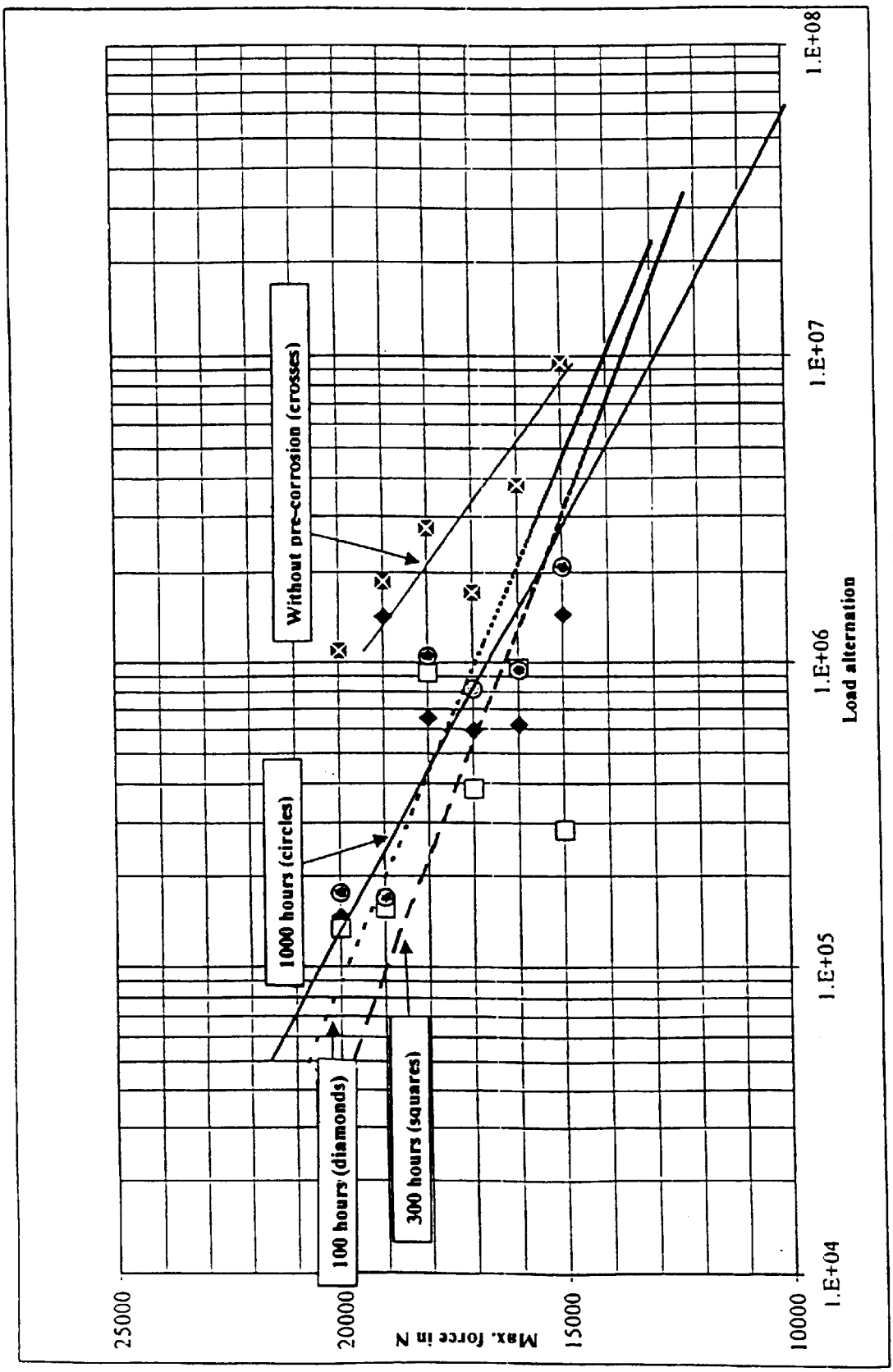
Fig. 8: Stress-number curves (3% NaCl solution) for different pre-corrosion periods

METHOD FOR DETERMINING THE FATIGUE STRENGTH OF A CORRODIBLE CONNECTING PART

BACKGROUND OF THE INVENTION

The invention relates to a method for determining the fatigue strength of a corrodible connecting part disposed between at least two overlapping construction parts, which connecting part, during its intended use, being subjected to a certain corrosive environment as well as to a predetermined, repeated mechanical stress, with the use of diagrams (stress-number curves) that illustrate the magnitude of the repeated stress as a function of the number of load repetitions, until the connecting part is destroyed.

The construction of multi-part machines, vehicles and the like requires the determination of the operating durability of connecting parts that hold together the individual parts under the stresses occurring during the intended use of the parts in order to preclude a premature failure. The material and/or the dimensions of the connecting parts should therefore assure a service life of, for example, at least 30 years under normal operating conditions.

The fatigue strength of connecting parts can be ascertained with the use of stress-number curves. In this test, the connecting part is subjected to a specified, repeated mechanical stress, and the number of stress cycles leading to the destruction of the connecting part is determined empirically. The stress-number curve indicates the respective number of stress cycles leading to destruction as a function of the magnitude of the repeated stress. The lower the stress, the less the dependency of the stress period on the stress. Steel materials that have resisted about $2 \times 10^6$ stress cycles are also not destroyed after further cycles if the stress remains unchanged, so the fatigue strength can be assumed. For aluminum materials, the fatigue strength begins after about $10^7$ stress cycles.

It is thus a relatively simple, fast process to determine the fatigue strength, that is, the maximum stress, of a connecting part without it being destroyed over a long period of time if the materials are not corroded. It is difficult, however, to ascertain the fatigue strength of corrodible connecting parts whose intended use subjects them to a certain corrosive environment. Corrosion can heavily influence fatigue strength. To this point, only certain corrosive environments were used to assess the effect of corrosion on the durability of a connecting part. One particular measure is the salt-spray fog test, in which a 3% NaCl solution is sprayed into the air while the connecting part is subjected to repeated mechanical stress.

A shortcoming of these tests, however, is that they do not allow for an extrapolation of the obtained values for a period of, for example, 30 years. In other words, it is not possible to determine the fatigue strength in a reasonable length of time. In addition, the tests are performed in standardized corrosive environments that often inadequately represent actual environments, so the obtained results are unusable.

DE 89 02 058 U1 discloses a method for determining the fatigue strength (compression-tension fatigue limit) of metallic materials that are exposed to repeated mechanical stresses in a certain corrosive environment.

DE-OS 16 73 274 describes a method for determining the fatigue strength of thick-walled semi-finished products that are exposed to a mechanical stress (tensile stress) in a certain corrosive environment.

Various connecting techniques are tested on a comparative basis through pre-corrosion and the recording of stress-number curves in E. Lachmann: Durability of bonded metal joints in motor vehicle construction, VIDE COUCHE MINCES, No. 272, Supp. S, August 1994–October 1994, pp. 277–283. A drawback of this investigation is that no dimension characteristic values can be determined, and the pre-corrosion period is very lengthy.

A similar method is described in Y. Oue et al.: Dependence of corrosion fatigue behaviour of friction-welded butt joints on friction welding procedure. Welding International, GB, Welding Institute, Abington, Vol. 10, No. 3, pp. 207–214. The pre-corrosion period is also unreasonably lengthy here.

A similar method is employed to test the resistance to vibration of base material and butt joints, as described in F.-J. Flossdorf et al.: Schwingfestigkeit wetterfester Baustähle nach langjähriger Bewitterung [Vibration Resistance of Weather-Proof Construction Steels after Long-Term Weathering]. Stahl und Eisen [Steel and Iron], DE, Verlag Stahleisen GmbH [publisher], Düsseldorf, Vol. 117 (1997), No. 11, pp. 105–111. Lengthy exposure to weather effects the pre-corrosion.

It is therefore the object of the present invention to improve a method for determining the fatigue strength of a corrodible connecting part between at least two overlapping construction parts, the part being subjected to a certain corrosive environment during its intended use, with diagrams (stress-number curves) showing the magnitude of the repeated stress as a function of the number of load repetitions up to the point of destruction of the connecting part, such that the actual corrosion conditions are more carefully considered and an extrapolation of the measured values is possible, so it can be determined within a short period of time whether a certain connecting part can withstand a certain stress in a certain corrosive environment over a period of, for example, 30 years.

SUMMARY OF THE INVENTION

In accordance with the invention, this object generally is accomplished by a method of the type described initially above wherein: stress-number curves are determined for test pieces for different, stress-free pre-corrosion periods; from the stress-number curves, the time after which the pre-corrosion period no longer affects the course of a subsequently-recorded stress-number curve is determined; afterward, a stress-free pre-corrosion of the connecting part is performed for a particular duration in an environment that corresponds to the defined corrosive environment, after which the duration of the pre-corrosion no longer affects the course of a subsequently-recorded stress-number curve; and, in order to record a stress-number curve, the pre-corroded connecting part is subsequently subjected to a predetermined, repeated mechanical stress in an environment that corresponds to the specific corrosive environment until the fatigue strength is attained. Advantageous modifications of the method in accordance with the invention are described.

For a specified period of time, the connecting part is subjected to a stress-free pre-corrosion in an environment that corresponds to the specified corrosive environment, after which the duration of the pre-corrosion virtually no longer influences the course of a subsequently-recorded stress-number curve. For recording a stress-number curve, the pre-corroded connecting part is then subjected to a predetermined, repeated mechanical stress in an environment that corresponds to the certain corrosive environment until the fatigue strength is attained. This occurs before the actual stress test. Consequently, the connecting part is already in such a corroded state that additional corrosion does not worsen the stability of the connection, that is, prior to the start of the stress test, the degree of corrosion that is the least favorable for the strength has already been attained. Surprisingly, it has been seen that this state can be attained after a relatively short period of time. Furthermore, because a corrosive environment that corresponds to the corrosive environment to which the connecting part is exposed during its intended use is selected for the pre-corrosion, a corrosion that corresponds to the corrosion during actual operation can be simulated; thus, more reliable values are obtained. In the subsequent stress test, stress-number curves that correspond to the stress-number curves for non-corroded connecting parts are obtained, which permits a problem-free extrapolation of a fatigue stress.

The pre-corrosion is preferably effected at a temperature higher than room temperature. This accelerates the corrosion, or shortens the pre-corrosion time; for example, at a temperature of 60° C., the pre-corrosion time can be reduced to about $1/10$ of the time at room temperature.

The invention is described below by way of exemplary embodiments illustrated in the figures.

BRIEF DESCRIPTION OF THE DRAWINGS

FIG. 3 is a diagram with stress-number curves for different corrosion media during the stress test.

FIGS. 4 & 5 are diagrams depicting the dependency of the fatigue-strength stresses from the pre-corrosion time for different corrosion media.

FIGS. 6, 7 & 8 are diagrams depicting stress-number curves of samples having pre-corrosion times of different lengths and different corrosion media.

DESCRIPTION OF THE PREFERRED EMBODIMENTS

Figure 1:
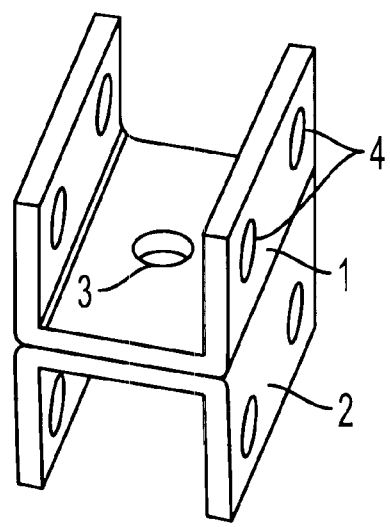
FIG. 1 shows a sample piece to be tested.

The sample piece according to FIG. 1 comprises two U pieces 1 and 2, which respectively have a bore 3 in their center leg. Superposing the center legs aligns the bores 3, so a rivet or a screw, for example, can pass through them and connect the two U pieces 1 and 2 to one another. Rivets are used as the connecting parts in the tests described below. Bores 4 in the legs of the two U pieces 1 and 2 serve as impact points for the forces that are repeatedly exerted on the connecting parts. The stress is a shearing force.

The strength of connecting parts that are to be used in a railway car was tested. To simulate the actual corrosion conditions, four corrosion zones, each being subjected to different corrosion media, were defined.

Figure 2:
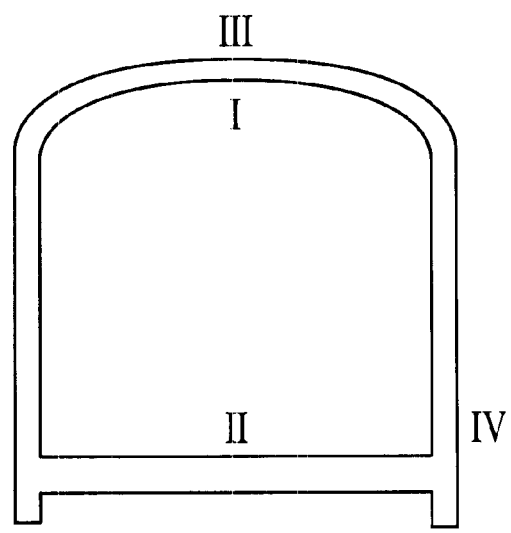
FIG. 2 is a schematic section through a railway car, for which a plurality of corrosion zones is defined.

As shown in FIG. 2, the zones I and II are inside the car, and the zones III and IV are located outside of the car. The zone I encompasses the interior of the car, with the exception of the floor region. Here, the corrosion media are air humidity and the condensation it forms. The zone II includes the floor region of the interior, in which the corrosion media are likewise humidity and condensation, as well as the cleaning agent used on the floor. The zone III is located outside of the car, specifically in the roof and undercarriage regions, while the zone IV is located on the outside of the car sides and the floor region.

The zones III and IV are subjected to considerably more severe corrosion than the zones I and II, because they are additionally exposed to airborne noxious substances ($SO_2$, $NO_x$, salts such as NaCl, acid rain, brake dust and the like), and are also treated with harsher cleaning agents. The mechanical procedure involved in cleaning the zone IV is more intensive than that for the zone III. The cleaning agents can be acidic or basic. The tested connecting parts were only intermittently subjected to the cleaning agents, as opposed to the other corrosive media, for better simulation of actual conditions.

First, stress tests were conducted, without pre-corrosion, on connecting parts comprising different materials. FIG. 3 shows the results for workpieces to be connected and the rivets connecting them, which respectively comprise AlMg-SiO.7 F26 (Al with 0.6% Si; 0.18% Fe; 0.13% Cu; 0.68% Mg; referred to hereinafter as "aluminum compound").

The stress tests were performed with a respective corrosive medium, namely water, an acidic cleaning agent, an alkaline cleaning agent and a 3% NaCl solution, that is conventionally used as a standard medium for corrosion tests. The tests were performed at 60° C., with the corrosive medium being circulated in a loop and sprayed onto the test pieces, or with the test pieces being immersed in the medium.

The number of stress cycles was $10^7$; the cycles were imposed upon the test pieces with a frequency of 30 to 40 Hz. The stress ratio was set at 0.5, that is, the upper stress point was at, for example, 20 kN, while the lower stress point was at 10 kN with an amplitude of 5 kN.

The obtained results demonstrate that the scatter of the values for air and water is very small, and significantly larger for the other corrosive media due to the non-homogeneous corrosion attacks. FIG. 3 shows the lines averaged from seven respective measurement points.

A comparison of the lines in FIG. 3 reveals that the NaCl solution and the alkaline cleaning agent have the most detrimental effect on the strength of the connecting part. In terms of the expected service life, there is a difference of an order of magnitude between a connecting part that is only exposed to water and one that is exposed to an alkaline cleaning agent or an NaCl solution.

FIGS. 4 and 5 illustrate the influence of the pre-corrosion period on the fatigue strength of an aluminum compound. In FIG. 4, the pre-corrosion was effected in humid (90%) air with a condensate formation at 60° C., and the stress period was $10^7$ cycles. The results shown in FIG. 5 are based on a pre-corrosion in an $SO_2$-containing atmosphere with 90% air humidity at 60° C., and with the influence of acidic and alkaline cleaners and a stress period of $10^7$ cycles. The respective measurement points represent the maximum strength after the respective stress period for a predetermined pre-corrosion period.

The pre-corrosion for the tests in accordance with FIG. 4 was effected under the above-described conditions, with the effect of the humid air (90% humidity) being present at 60° C. Here, the temperature was alternately held at 60° C. and 50° C. for two hours at a time so that the influence of a condensation of the air humidity could also be assessed.

If the values obtained for 60° C. are extrapolated for a temperature of 25° C., which more closely corresponds to actual conditions, a pre-corrosion period that is about ten times longer is calculated. This results from the Arrhenius law, according to which the speed of corrosion increases by a factor of two for every 10° C. increase in the temperature. A corrosion period of, for example, 100 hours at 60° C. thus corresponds to a corrosion period of 1000 hours at 25° C.

The illustrated results show that the fatigue strength does not decrease continuously as the pre-corrosion period lengthens, but, surprisingly, that as of a specific pre-corrosion period, the fatigue strength remains nearly constant. The fact that the fatigue-strength value for 1000 hours is somewhat higher than for 300 hours in FIG. 4, and is higher for 1000 hours and 300 hours than for 100 hours in FIG. 5, is not attributed to an increase in the fatigue strength, but to the relatively large scattering of the measured values.

It can be seen clearly, however, that with a pre-corrosion in humid air for more than 300 hours, the fatigue strength no longer drops perceptibly, and with a pre-corrosion in an $SO_2$-containing atmosphere with 90% humidity and condensation, as well as the influence of acidic and alkaline cleaning agents, this effect is already apparent after 100 hours. Therefore, it is possible within a relatively short period of time to project the impact of the corrosion on the fatigue strength of a connecting part for its expected service life, e.g., 30 years. As shown, the testing length can be significantly reduced by an increase in the temperature.

Finally, FIGS. 6, 7 and 8 illustrate stress-number curves for aluminum connecting parts for different corrosive media, and different pre-corrosion periods. FIG. 6 relates to a pre-corrosion in an interior atmosphere at 60° C. with 90% humidity and condensation, and a stress test performed at 60° C. FIG. 7 depicts a pre-corrosion under the influence of an $SO_2$-containing atmosphere at 60° C. with 90% humidity, and under the influence of spray-application alkaline and acidic cleaning agents at 60° C., and a stress test performed with a liquid, alkaline cleaning agent at 25° C. FIG. 8 illustrates a pre-corrosion performed under the, influence of a spray-application 3% NaCl solution at 60° C. and a stress value [sic] with a 3% NaCl solution at 25° C. The corrosion conditions in FIG. 6 correspond approximately to those in zone I in FIG. 2 and those in zones III and IV in FIG. 7. The illustrated curves were obtained for connecting parts that were not pre-corroded, and those that were subjected to pre-corrosion for 100 hours, 300 hours and 1000 hours, respectively.

It can be seen from FIG. 6 that the fatigue strength diminishes as the pre-corrosion period increases, but that this is only the tendency up to about 300 hours, at which point the fatigue strength is extensively independent of the pre-corrosion period. The relatively wide scattering that can be ascertained with lengthy pre-corrosion periods presumably results from local attacks, which can vary among the individual test pieces.

For determining the fatigue strength of an aluminum connecting part, under the above-described corrosion conditions, it suffices to limit the pre-corrosion time to 300 hours.

The fatigue-strength values in FIG. 7 are clearly lower than those in FIG. 6. It is, however, also apparent and even more clearly identifiable that only a short pre-corrosion period is necessary for determining the fatigue strength of a connecting part under the given corrosion conditions. Here, the stress-number curve for a pre-corrosion period of 100 hours is even lower than for 300 hours, and even for 1000 hours. This can, however, again be attributed to the scattering of the measured values. It is therefore evident that even a pre-corrosion period of 100 hours at 60° C. suffices to ascertain the fatigue strength of an aluminum connecting part.

FIG. 8 illustrates similar values, except that a 3% NaCl solution is used as the corrosion medium instead of an alkaline cleaning agent, with the test piece being immersed in the solution during the stress test. The stress-number curves for the pre-corrosion times of 100 hours, 300 hours and 1000 also extensively coincide here, so the pre-corrosion can likewise be halted after 100 hours, because a longer period does not reveal additional details about the fatigue strength.

Tests were also performed with stainless-steel connecting parts, which tended to yield the same results. Because, however, the effect of corrosion is much stronger in aluminum connecting parts than in steel connecting parts, the description of the exemplary embodiments for clarifying the invention was oriented toward aluminum connecting parts.

The above-described method permits the influence of corrosion on the strength of a connecting part to be ascertained within a relatively short period of time, thereby allowing for an extrapolation for a fatigue strength over, for example, 30 years and beyond. The use of corrosive media that extensively correspond to the media that act on the connecting part during actual operation can increase the precision of the procedure. The method is therefore a valuable tool in constructing connecting parts that are intended to have a specific service life, provided that the mechanical stresses and corrosive environment to which they will be subjected to during use are known.

What is claimed is:

1. A method for determining the fatigue strength of a corrodible connecting part between at least two overlapping construction parts, the connecting part being subjected to a defined corrosive environment during its intended use, as well as a predetermined, repeated mechanical stress, with the use of diagrams (stress-number curves) that illustrate the magnitude of the repeated stress as a function of the number of load repetitions until the connecting part is destroyed, comprising:

determining stress-number curves for test pieces that have been previously subjected to a corrosive environment corresponding to said defined corrosive environment for different, stress-free pre-corrosion periods;

from said stress-number curves determining, a particular duration of pre-corrosion after which the pre-corrosion period no longer affects the course of a subsequently-recorded stress-number curve;

afterward, performing a stress-free pre-corrosion of the connecting part for a particular duration of pre-corrosion in an environment that corresponds to said defined corrosive environment; and, in order to record a stress-number curve, subsequently subjecting the pre-corroded connecting part to a predetermined, repeated mechanical stress in an environment that corresponds to the specific corrosive environment until the fatigue strength is attained.

2. The method according to claim 1, including performing the pre-corrosion at a temperature that is higher than room temperature.

3. The method according to claim 2, wherein the pre-corrosion is performed at 60° C.

4. The method according to claim 1, including using said method for testing the fatigue strength of connecting parts to be used in a railway car.

5. The method according to claim 4, including dividing the corrosive environment of the railway car into a plurality of zones that are subjected to different levels of corrosion.

6. The method according to claim 5, further comprising determining the zones as a function of the internal or external atmosphere, as well as the respective cleaning agents used.

7. The method according to claim 1, including for performing the pre-corrosion, spraying a liquid, corrosive medium onto the connecting part, and immersing the connecting part in the corrosive medium for performing the stress test.

8. The method according to claim 1, including selecting air as the corrosive environment, and maintaining a specific air humidity and setting the air temperature such that intervals with and without the formation of condensation alternate.

9. The method according to claim 1, wherein pre-corrosion of at least one of the test piece and the connecting part is performed at a temperature that is elevated with respect to the temperature during the intended use of the connecting part.

10. A method for determining the fatigue strength of a corrodible connecting part between at least two overlapping construction parts used in a railroad car, with the connecting part, during its intended use, being subjected to a certain corrosive environment as well as to a predetermined, repeated mechanical stress, with the use of diagrams (stress-number curves) that illustrate the magnitude of the repeated stress, as a function of the number of load repetitions, until the connecting part is destroyed, comprising:

dividing the corrosive environment of the railroad car into a plurality of zones that are subjected to different levels of corrosion;

determining stress-number curves for test pieces for different, stress-free pre-corrosion periods;

from the stress-number curves, determining the time after which the pre-corrosion period no longer affects the course of a subsequently-recorded stress-number curve;

afterward, performing a stress-free pre-corrosion of the connecting part for a particular duration in an environment that corresponds to the defined corrosive environment, after which the duration of the pre-corrosion no longer affects the course of a subsequently-recorded stress-number curve; and, in order to record a stress-number curve, subsequently subjecting the pre-corroded connecting part to a predetermined, repeated mechanical stress in an environment that corresponds to the specific corrosive environment until the fatigue strength is attained.

11. The method according to claim 10, including determining the zones as a function of the internal or external atmosphere, as well as the respective cleaning agents used.

* * * * *